United States Patent
Kohlheb et al.

[11] Patent Number: 6,059,970
[45] Date of Patent: May 9, 2000

[54] MEMBRANE SEPARATION DEVICE

[76] Inventors: Robert Kohlheb, Maisfeld 12, D-29336 Nienhagen, Germany; Robert Rautenbach, Wolfhaag 62, NL 6291 N Vaals, Netherlands

[21] Appl. No.: 09/013,740

[22] Filed: Jan. 27, 1998

[30] Foreign Application Priority Data

Jan. 28, 1997 [DE] Germany ............... 197 02 902

[51] Int. Cl.[7] ............... B01D 63/00
[52] U.S. Cl. ............... 210/321.6; 210/321.78; 210/323.2; 210/359; 210/380.1; 210/350; 210/354; 210/355; 210/331
[58] Field of Search ............... 210/323.2, 324, 210/359, 364, 355, 356, 380.1, 321.6, 350, 354, 416, 413, 331, 407, 321.78

[56] References Cited

U.S. PATENT DOCUMENTS

| | | | |
|---|---|---|---|
| 4,308,142 | 12/1981 | Braukmann et al. | 210/355 |
| 4,655,911 | 4/1987 | Tabor | 210/354 |
| 4,702,842 | 10/1987 | Lapierre | 210/651 |
| 4,795,570 | 1/1989 | Young | 210/355 |

FOREIGN PATENT DOCUMENTS

| | | |
|---|---|---|
| 0448466 | 9/1991 | European Pat. Off. |
| 0605826 | 7/1994 | European Pat. Off. |
| 2420728 | 11/1974 | Germany |
| 4143423C2 | 10/1992 | Germany |

*Primary Examiner*—Ana Fortuna
*Attorney, Agent, or Firm*—Harold A. Burdick

[57] ABSTRACT

A membrane separation device is disclosed having a cylindrical membrane support (4), which is sealed off between a top plate (26) and a bottom plate (28), whereon the cylindrical outer surface of the membranes support a membrane (6) is located, and which is surrounded by cylindrical components (14, 8) which are sealed off in the top plate and bottom plate thereby forming a cylindrical ring area (16). Permeate collection bores (20) communicate with the membrane through the membrane support and are connected with a permeate draw off connection (60). The suction side of a circulation pump (44) is connected with an enclosed inner chamber (47) formed by the cylindrical membrane support. The outer ring area is connected to the pressure side of the circulation pump and communicates with the inner chamber through a circulation channel (54). The inner chamber is connected to a infeed connection (58). The circulation pump communicates with a draw off (64) on the pressure side for the extraction of concentrate.

20 Claims, 2 Drawing Sheets

MEMBRANE SEPARATION DEVICE

FOREIGN PRIORITY

This Application claims priority under the Paris Convention for the Protection of Industrial Iroperty based upon German Patent Application No. 197 02 902.7 filed on Jan. 28, 1997 in the German Patent Office in Munchen, Germany.

FIELD OF THE INVENTION

The invention is relates to membrane-type separation devices, and, more particularly, relates to membrane separation devices for simulation of filtration and permeation processes, and related investigations.

BACKGROUND OF THE INVENTION

There are membrane separation devices known, which allow the simulation of filtration processes as well as permeation processes. Often they are employed in a batch-process mode, whereby the to be tested medium after throttling of the system pressure is recirculated into an atmospheric container as retentate. The system pressure built up is almost with no exception provided by means of high pressure pumps.

Known membrane separation devices utilize flat membranes in circular or square cut forms which are employed in a two-dimensional surface plane. These known devices are employed in test cells, which arc commonly used for Membrane technical investigations such as cross flow, and pressure filtration. The test celes consist of a two part pressure housing, with the flat membrane supported between the upper and lower housing parts. The membrane itself typically rests on a filter support structure which is equipped with a flow channel, with the opening into the test cell oriented toward the membrane. The ends of flow channels are connected to a feed nozzle and concentrate draw off nozzle, respectively.

In these heretofore known test cells, the filtrate is directed away through a flow channel which) is operatively associated with the membrane. Through the feed nozzle the conglomerate material is introduced perpendicular onto the membrane, and the conglomerate material is escorted away over the concentrate draw off nozzle, also perpendicularly. To protect the membrane from wear of the feed flow impact, deflector plates are installed between the feed flow nozzle and membrane. Flow against the membrane is guided in a parallel, spiral or meandering course over the membrane.

In such known pilot test cells, the membrane surface cannot be utilized altogether satisfactorily for medium separation, up to about 35% of the membrane surface remaining unusable. Such unoptimized membrane utilization works as a disadvantage for throughput evaluation of the pilot test cell. Therefore, a very reluctant upconcentration is shown. This results in time wasted, an unnecessary superheating of the medium (without underpressure circulation), and, under certain circumstances, requires an additional cooling or tempering step.

Furthermore, it is known of typical mediums to be investigated that they are subject to transporting limitations. For example, typical mediums wherein use of such a test cell is advantageous are often viewed as dangerous goods (i.e., hazardous materials subject to transport limitations), have high organic content which may cause bacteriological contamination during the time of transportation and therefore a distinct alteration in the nature of the medium, and/or are toxic and originally located in a foreign country raising problem with border crossing. Moreover, return transport or disposal (often as hazardous waste) of the already tested medium is expensive. These complications are magnified since heretofore known testing devices typically require more than 100 Liters of the medium for the purpose of such membrane technical investigations. Such transportation and disposal difficulties could be improved Rout for the limited mobility of the test units themselves (thus limiting availability of field testing).

Further improvements of such membrane test units could thus be utilized directed to making thee units relatively more light weight, transportable i.e., mobile), and capable of faster and more reliable investigation of environmentally relevant materials.

SUMMARY OF THE INVENTION

This invention provides a membrane separation device that is compact and mobile, and which does not require a pressure boosting pump. The material flow at the membrane is provided utilizing an under-pressure operable circulation pump. The pump is configured so that liquids with higher salt contents (up to about 15% by weight) can be pumped. The device is effective with relative small test volumes (for example 100 ml), whereby a fast upconcentration, and therefore a short test lime, is feasible. The dead volume of the unit is kept small (under 1%) since all chambers, areas and channels accommodate material flow. Superheating of the substance to be investigated is negligible since pressure differentials during circulation in the device are very small (maximum about 0.5 bar), and with the working pressure adjusted through an external pressure source (for example, a gas bottle).

The device of this invention is especially suited for the following membrane separation processes: microfiltration (separation of micro-particles of suspensions); ultrafiltration (separation of molecular portions or of emulsions); diafiltration (retaining of molecules and removal of saline or alcoholic phases from watery solutions); nanofiltration (molecular and ionic fractionacion), and; reverse osmosis (removal of organic solutions and upconcentration of saline waters).

The device is well suited for use at the site of the material to be tested (i.e., for field tests, and, therefore, fast track analysis of membrane technical separation capability for burdened substances of watery solution is considerably improved.

The device of this invention is suitable for the testing of a variety of different burdened liquid materials (for example industrial waste water disposal, leach water, ground water, soil washing waste water, subterranean water, surface water, river water, etc.) and may find particular applicability in the following cases: petrochemical process water: 5% Chlopropanol and 1.8% HCL; technological waste water from chemical industry: 2.4% Chlorphenol, 5% NaCL; waste water from groung remediation or soil washing of military objectives: oil, detergent, residual-simulation after the employment of ABC weapons; waste water from regeneration processes of ion exchanger: mostly NaCL, salts at higher concentrations; processing of laundry waste water, and; galvanic waste water and rinse bath recycling: heavy metals ark $H_2O$.

The membrane separation device includes a cylindrical membrane supported in a housing defining a chamber internal the cylindrical membrane and an outer ring area extending around the cylindrical membrane opposite thereof from the chamber. The chamber has a material feed connection thereto and a circulation channel connects the chamber and the outer ring area. A pump is Provided for inducing material circulation between the chamber and the outer ring area and is connected with a concentrate draw off, a permeate collector having a permeate draw off being positioned adjacent to the membrane for collection of permeate passed through the membrane from the material flow.

The membrane is supported on a cylindrical support positioned between a top plate and a bottom plate of the housing at an outer cylindrical surface of the cylindrical support, and a surrounding cylindrical component spaced from the cylindrical membrane and positioned between the top plate and the bottom plate defines the cylindrical outer ring area.

The membrane support has bores therein defining the permeate collector, with the bores in communication with the membrane, and a permeate draw off connection connected with the permeate collection bores. The circulation pump is, on its suction side, connected with the inner chamber and, on its pressure side, is connected with the outer ring area and with a draw off for extraction of concentrate. A cylindrical spacer surrounds the membrane, the cylindrical spacer radially loaded by a cylindrical spiral. An inner ring area is defined between the cylindrical spiral and the membrane, the inner ring area connected between the pressure side of the circulation pump and the circulation channel.

It is therefore an object of this invention to provide an improved membrane separation device.

It is another object of this invention to provide a membrane separation device that is compact and portable, that requires no pressure boosting pump for operation, that efficiently operates on small test volumes, and that provides accurate test results.

It is still another object of this invention to provide a membrane separation device that mates efficient use of the membrane surface by providing a cylidrical membrane surface.

It is yet another object of this invention to provide a membrane separation device including a cylindrical membrane, housing means for supporting the membrane therein and thus defining a chamber internal the cylindrical membrane and an outer ring area extending around the cylindrical membrane opposite thereof from the chamber the chamber having a material feed connection thereto a circulation channel connecting the chamber and the outer ring area, a pump for inducing material flow between tile chamber and the outer ring area and connected with a concentrate draw off, and permeate collection means having a permeate draw off and positioned adjacent to the membrane for collection of permeate passed through the membrane from the material flow.

It is still another object of this invention to provide a membrane separation device including a cylindrical membrane support positioned between a top plate and a bottom plate and forming an inner chamber, the inner chamber having an intake feed connection, a cylindrical membrane positioned at an outer cylindrical surface of the cylindrical membrane support and between the top plate and the bottom plate, a surrounding cylindrical component spaced from the cylindrical membrane and positioned between the top plate and the bottom plate to form a cylindrical outer ring area, the outer ring area connected to the inner chamber by a circulation channel, the membrane support having permeate collection bores thereat in communication with the membrane, a permeate draw off connection connected with the permeate collection bores, and a circulation pump which is on its suction side connection with the inner chamber and on its pressure side with the outer ring area, the inner chamber receiving through the intake feed connection a substance of interest, the pressure side of the circulation pump connected with a draw off for extraction of concentrate.

It is still another object of this invention to provide a membrane separation device having a cylindrical spacer surrounding the membrane, the cylindrical spacer radially loaded by a cylindrical spiral, an inner ring area being defined between the cylindrical spiral and the membrane, the inner ring area connected between the pressure side of a circulation pump and a circulation channel between an inner chamber and an outer ring area of the device.

With these and other objects in view, which will become apparent to one skilled in the art as the description proceeds, this invention resides in the novel construction, combination, and arrangement of parts substantially as hereinafter described, and more particularly defined by the appended claims, it being understood that changes in the precise embodiment of the herein disclosed invention are meant to be included as come within the scope of the claims.

BRIEF DESCRIPTION OF THE DRAWINGS

The accompanying drawings illustrate a complete embodiment of the invention according to the best mode so far devised for the practical application of the principles thereof, and in which.

DESCRIPTION OF THE INVENTION

Figure 1:
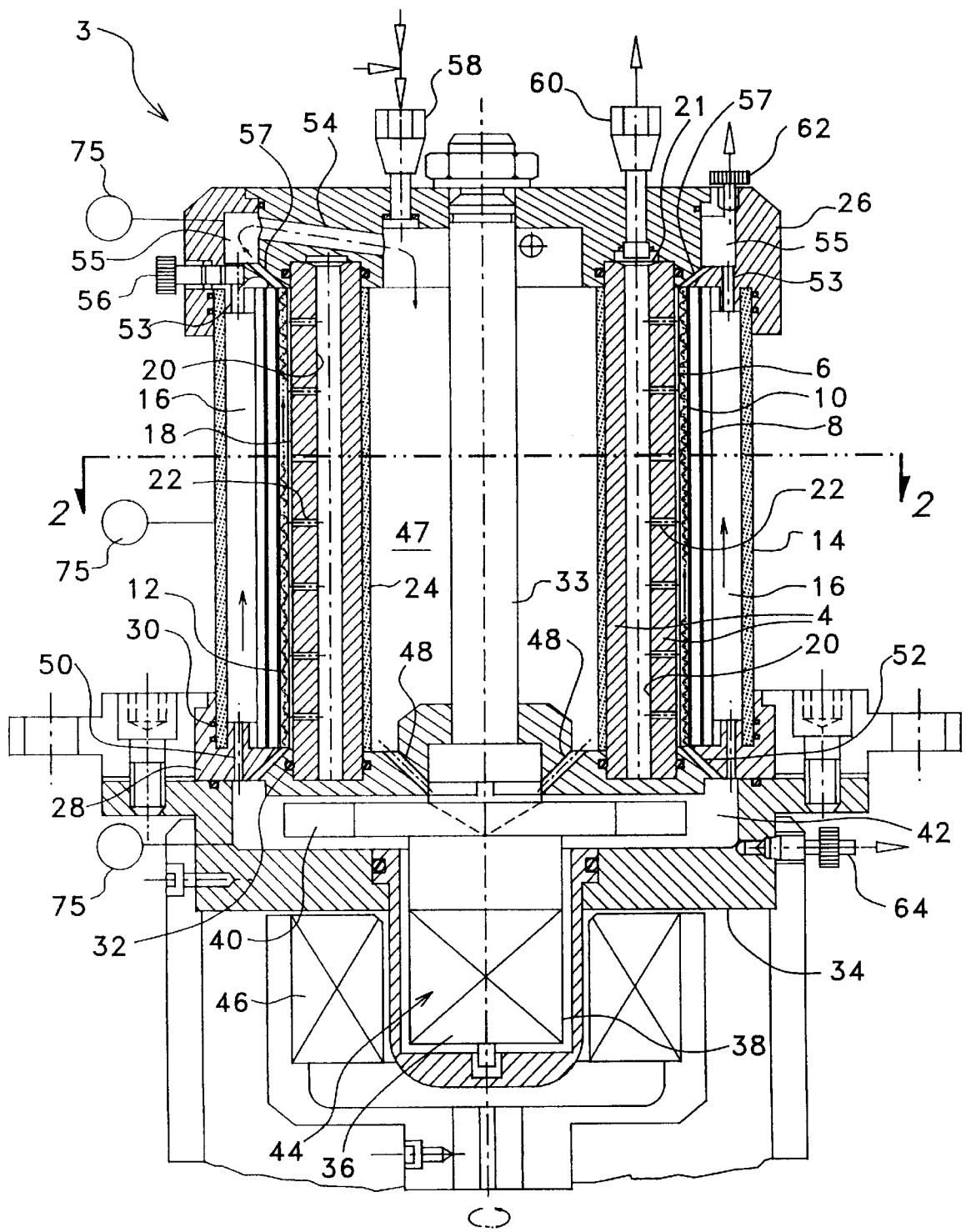
FIG. 1 is a vertical cross sectional illustration of the membrane separation device of this invention.

The drawings show a membrane separation unit 3 with cylindrical membrane support 4 (preferably made of synthetic material) on which cylindrical membrane 6 is positioned at the outer cylindrical surface thereof, therefore providing a three dimensional membrane. Spaced around the membrane is cylindrical spiral 8 preferably a foil made from synthetic material) however, cylindrical spiral 8 spaced away from the membrane by means of cylindrical spacer holder 10, spacer holder 10 being clamped around membrane 6 by spiral 8. Spacer holder 10 is configured as a turbulence creating device (i.e., inducing turbulent flow between membrane 6 and spiral 8) at the thus formed inner cylindrical ring room, or area, 12.

Cylindrical spiral 8 is surrounded by and space from outer cylinder 14 (preferably made from metal), so that between cylinder 14 and spiral 8 an outer cylindrical ring room, or area, 16 is defined.

Cylindrical membrane support 4 is, through cylindrical jacket 18, drilled in an axial direction with through-going permeate collection bores 20, which bores 20 each connect with a plurality of transverse bores 22 in cylinder jacket 18 communicating with membrane 6 and thus with outer ring room 16. On the inner surface of membrane support 4 is cylindrical support body 24, preferably made from metal.

The cylindrical arrangement of the device, including cylindrical support body 24, membrane support 4, spacer holder 10, spiral 8 and cylinder 14, is maintained between top plate 26 and bottom plate 28, outer cylinder 14 and cylindrical membrane support 4 being sealed off in the top and bottom plates by means of O-rings 30 and 32, respectively. The top and bottom plates are braced and fasten to each other by means of central bolt 33, an overall housing for the device thus being defined by outer cylinder 14 and plates 26 and 28.

Underneath bottom plate 28 is flanged on pump housing 34, within which is rotor 36, located in rotor chamber 38, and pump impeller 40, located in impeller chamber 42, of circulation pump 44. Rotor 36 is preferably coupled by permanent magnet coupling 46. The pump is driven by an electric motor (not shown).

Inwardly from cylindrical membrane support 4 and cylindrical support body 24, enclosed inner room, or chamber, 47 is defined and connected through at least one of the bores 48 in bottom plate 28 with the suction side of impeller room 42. To the peripheral pressure (discharge) side of impeller room 42, outer ring room 16 is connected through flow bores 50 and, through flow bores 52, with inner ring room 12.

Outer ring room 16 is flow connected with inner chamber 47 by bores 53 to ring shaped channel 55 and at least one circulation channel 54 therefrom formed in top plate 26. The flow velocity in outer ring room 16 is adjustable by means of adjustment screw 56 (with reference to pressure gauges 75), by which the cross sectional flow through bore 53 is adjusted. Inner ring room 12 having spacer holder 10 thereat is flowably connected through bores 57 with ring shaped channel 55.

Through intake feed connection 58, continuously or discontinuously the to be to investigated medium, for example contaminated water, flows through top plate 26 into inner chamber 47, preferably under valve control (not shown). The medium may be further pressurized through feed connection 58 by means of air or nitrogen.

Continuous permeate draw-off is provided through draw-off and vacuum connection 60 interconnected with collection bores 20. Outer ring room 16 may be vented (for deaeration) through vent 62. At impeller chamber 42, located on the pressure side, is concentrate draw-off connection 64.

Figure 2:
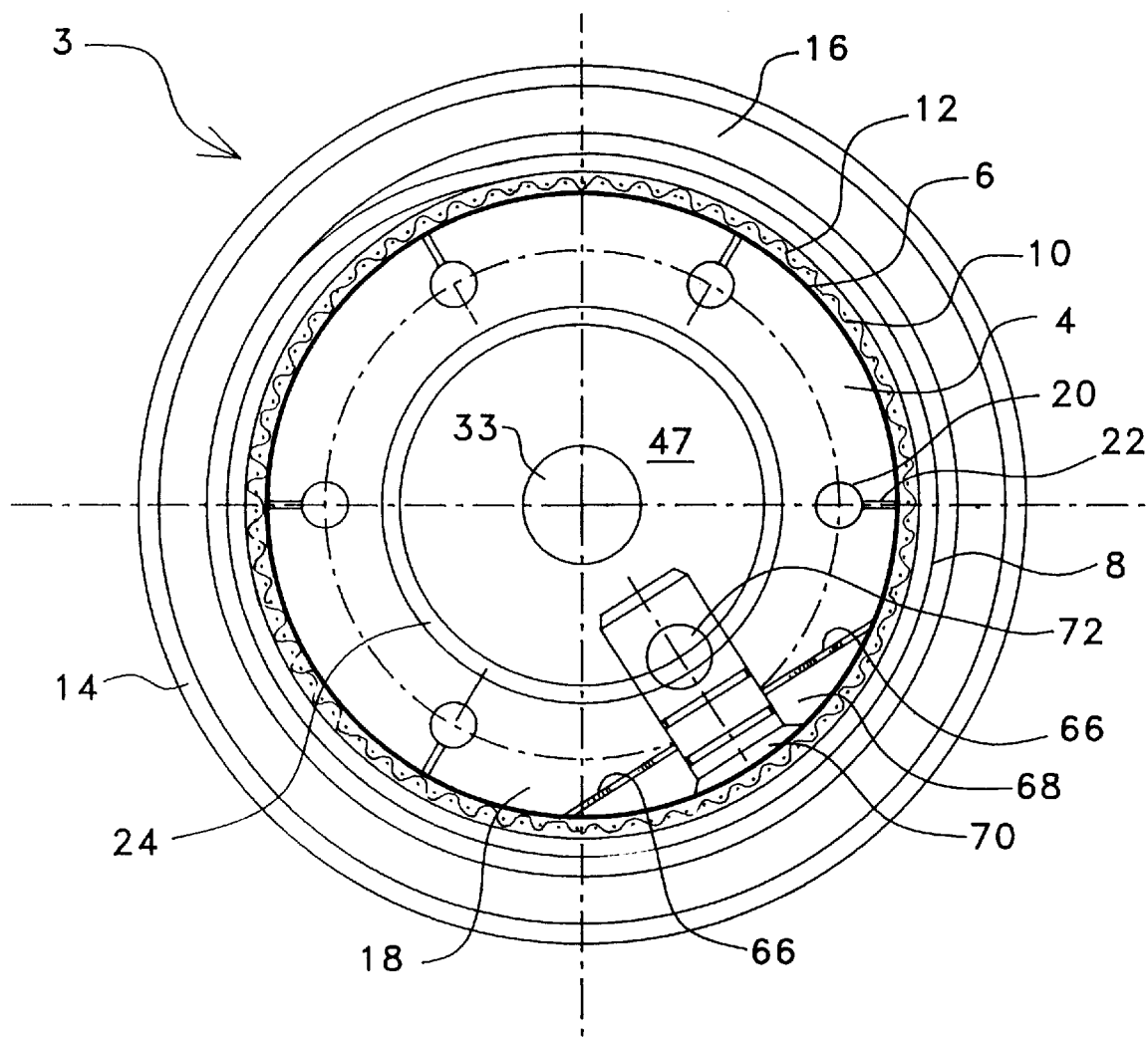
FIG. 2 is a cross section taken through section lines 2—2 of FIG. 1.

To fasten membrane 6 to cylindrical membrane support 4, the latter has a flattened area 66 on its outer surface (see FIG. 2), against pressure plate 68 (which has a cylindrical sectional shape), and which is capable of being pressed by means of at least two tension bolts 70. Tension bolts 70 pass through pressure plate 68 and jacket 18 of membrane support 4, whereby tension bolts 70 exert pressure by means of eccentric activation 72 thereby fastening and sealing membrane 6 between flattened area 66 and pressure plate 68.

In use, the to be tested burdened (typically watery) medium is introduced through feed connection 58 into inner chamber 47 (with a working pressure, for example typically between about 3 to 60 bar, and up to 240 bar for a higher yield, working pressure control by means of pressurized air or inert gas pressure). The medium passes through bores 48 into circulation pump 44 and through bores 50 and 52 into outer ring room 16 and into inner ring room 12, whereafter the substance goes again into inner chamber 47 through bores 53 and 57, ring channel 55 and circulation channel 54.

Because of increasing pressure in outer ring room 16, spiral 8 is pressed against cylindrical spacer holder 10, which therefore presses membrane 6 against cylindrical membrane support 4. Cross-flow sections are chosen or adjusted (using adjustment screw 56), such that the flow velocity in outer ring room 16 (for example, from between about 0.0 to 0.09 m/sec.) is smaller than the flow velocity in inner ring room 12 (for example, from between about 0.5 to 5 m/sec.).

Due to the working pressure, at least a portion of the permeate is pressed through membrane 6, passing by transverse bores 22 into permeate collection bores 20. From there, the permeate can be drawn off continuously or discontinuously through draw-off and vacuum (connection 60. The thereafter upconcentrated medium is recirculated and can be drawn off through concentrate draw-off connection 64. Additional medium may be fed through feed connection 58 in amounts equivalent to amounts of permeate being drawn off.

For use in this device, membrane 6 may be any of the known membrane materials utilized for the particular testing operation (for example, polysulthone (PSO) UF or MF membranes, cellulose acetate RO, NF or UF membranes, thin film composite RO or NF membranes membranes (TFC or TFM, for example), PVDF membranes, PAN membranes, ceramic membranes, and the like). Spiral 8 may be made of synthetic foil material having a thickness of between about 0.2 to 2 mm (for example PVDF or PVA material). Spacer holder 10 is preferably made of a synthetic polymeric material (selected for compatibility with the tested medium) in a diamond, parallel or other spacer arrangement configuration.

What is claimed is:

1. A membrane separation device comprising:
   a cylindrical membrane support positioned between a top plate and a bottom plate and forming an inner chamber, said inner chamber having an intake feed connection;
   a cylindrical membrane positioned at an outer cylindrical surface of said cylindrical membrane support and between said top plate and said bottom plate;
   a surrounding cylindrical component spaced from said cylindrical membrane and positioned between said top plate and said bottom plate to form a cylindrical outer ring area, said outer ring area connected to said inner chamber by a circulation channel;
   said membrane support having permeate collection bores thereat in communication with said membrane, a permeate draw off connection connected with said permeate collection bores; and
   a circulation pump which is on its suction side connected with said inner chamber and on its pressure side with said outer ring area, said inner chamber receiving through said intake feed connection a substance of interest, said pressure side of said circulation pump connected with a draw off for extraction of concentrate.

2. The membrane separation device of claim 1 wherein said collection bores are positioned axially in said membrane support, said collection bores communicating with said membrane through leading bores in said outer surface of said membrane support.

3. The membrane separation device of claim 1 further comprising a cylindrical spacer surrounding said membrane, said cylindrical spacer radially loaded by a cylindrical spiral, an inner ring area being defined between said cylindrical spiral and said membrane, said inner ring area connected between said pressure side of said circulation pump and said circulation channel.

4. The membrane separation device of claim 3 wherein said pressure side of said circulation pump is connected through bores formed in said bottom plate with said outer and said inner ring areas, and wherein said suction side of said circulation pump is connected through bores formed in said bottom plate with said inner chamber.

5. The membrane separation device of claim 3 wherein said spacer 10 is shaped as a turbulence creating device for through flowing substance in said inner ring area.

6. The membrane separation device of claim 3 wherein said top plate includes a ring channel formed therein which is connected through said circulation channel with said inner chamber and by bores in said top plate with the said outer and said inner ring areas.

7. The membrane separation device of claim 6 further comprising flow velocity adjusting means adjacent said circulation channel for controlling floor velocity in said ouster ring area.

8. The membrane separation device of claim 7 wherein said flow velocity adjusting means controls flow velocity in a range wherein flow velocity in said outer ring area is lower than in said inner ring area.

9. The membrane separation device of claim 1 wherein said circulation pump is powered by an electric motor through a permanent magnetic coupling.

10. The membrane separation device according of claim 1 wherein said cylindrical membrane support includes a cylindrical support body adjacent said inner chamber.

11. The membrane separation device of claim 1 wherein said top plate and said bottom plate are connected with coach other by a central connector.

12. The membrane separation device of claim 1 further comprising a vent connected with said outer ring area for selective deaeration of said outer ring area.

13. A membrane separation device comprising:

a cylindrical membrane;

housing means for supporting said membrane therein and thus defining a chamber internal said cylindrical membrane and an outer ring area extending around and spaced from said cylindrical membrane opposite thereof from said chamber, said chamber having a material feed connection thereto;

an inner ring area defined in said housing adjacent to said membrane;

a circulation channel connecting said chamber and said outer ring area;

a pump having a pressure side operationally connected with said outer ring area and a suction side operationally connected with said chamber for inducing material flow between said chamber and said outer ring area, said inner ring area connected between said pressure side of said pump and said chamber, said pump connected with a concentrate draw off; and permeate collection means having a permeate draw off and positioned adjacent to said membrane for collection of permeate passed through said membrane from said material flow.

14. The membrane separation device of claim 13 wherein said permeate collection means is defined axially adjacent to said membrane and communicate wish said membrane through lateral bores opening to said membrane.

15. The membrane separation device of claim 13 further comprising a cylindrical spacer surrounding said membrane and means for radially loading said cylindrical spacer responsive material flow pressure, said inner ring area being defined between said loading means and said membrane by said spacer.

16. A membrane separation device comprising:

a cylindrical membrane;

housing means for supporting said membrane therein and thus defining a chamber internal said cylindrical membrane and an outer ring area extending around and spaced from said cylindrical membrane opposite thereof from said chamber. said chamber having a material feed connection thereto;

an inner ring area defined in said housing adjacent to said membrane;

a ring channel formed in said housing and connected through a circulation channel with said chamber and by bores in said housing with said outer and said inner ring areas;

a pump for inducing material flow between said chamber and said outer ring area and connected with a concentrate draw off, said inner ring area connected between a pressure side of said pump and said chamber; and permeate collection means having a permeate draw off and positioned adjacent to said membrane for collection of permeate passed through said membrane from said material flow.

17. The membrane separation device of claim 16 further comprising flow velocity adjusting means adjacent said circulation channel for controlling flow velocity in said outer ring area in a range wherein flow velocity in said outer ring area is lower than in said inner ring area.

18. The membrane separation device of claim 16 wherein said permeate collection means is defined axially adjacent to said membrane and communicates with said membrane through lateral bores opening to said membrane.

19. The membrane separation device of claim 16 further comprising a cylindrical spacer surrounding said membrane and means for radially loading said cylindrical spacer responsive material flow pressure, said inner ring area being defined between said loading means and said membrane by said spacer.

20. The membrane separation device of claim 16 wherein said pressure side of said pump is operationally connected with said outer ring area, and wherein a suction side of said pump is operationally connected with said chamber.

* * * * *